United States Patent
Yeh et al.

(10) Patent No.: US 9,387,057 B2
(45) Date of Patent: Jul. 12, 2016

(54) CERAMIC ARTICLES WITH INCREASED SURFACE ROUGHNESS AND METHODS FOR MANUFACTURING THE SAME

(71) Applicants: MACKAY MEMORIAL HOSPITAL, Taipei (TW); NATIONAL TAIPEI UNIVERSITY OF TECHNOLOGY, Taipei (TW)

(72) Inventors: Shu-Tuan Yeh, Taipei (TW); Yung-Chin Yang, Taipei (TW); Pei-Chi Hsu, Taipei (TW)

(73) Assignees: MACKAY MEMORIAL HOSPITAL, Taipei (TW); NATIONAL TAIPEI UNIVERSITY OF TECHNOLOGY, Taipei (TW)

(*) Notice: Subject to any disclaimer, the term of this patent is extended or adjusted under 35 U.S.C. 154(b) by 0 days.

(21) Appl. No.: 14/516,225

(22) Filed: Oct. 16, 2014

(65) Prior Publication Data
US 2015/0037494 A1 Feb. 5, 2015

Related U.S. Application Data

(62) Division of application No. 13/562,548, filed on Jul. 31, 2012, now abandoned.

(30) Foreign Application Priority Data
Feb. 17, 2012 (TW) .............................. 101105381 A (51) Int. Cl.
*A61C 7/16* (2006.01)
*A61C 13/083* (2006.01)
(Continued)

(52) U.S. Cl.
CPC ................. *A61C 13/083* (2013.01); *A61C 5/08* (2013.01); *A61C 13/0003* (2013.01); *B32B 5/02* (2013.01);
(Continued)

(58) Field of Classification Search
CPC .......................................................... A61C 7/16
USPC ................................................ 427/2.29; 433/9
See application file for complete search history.

(56) References Cited

U.S. PATENT DOCUMENTS 4,820,545 A * 4/1989 Negrych .................. A61C 7/12
216/101
5,077,132 A * 12/1991 Maruno ............... A61K 6/0273
424/602

(Continued)

FOREIGN PATENT DOCUMENTS

| DE | 102009051655 B3 * | 12/2010 | ............... A61C 5/10 |
| SE | WO 2010145822 A1 * | 12/2010 | ............ C04B 41/009 |
| WO | WO 2010/145822 | 12/2010 | |

OTHER PUBLICATIONS

ZIrconnect Product. retreived from http://www.kuss-dental.es/en/productos_zirconnect.html.*
(Continued)

*Primary Examiner* — Cachet Sellman
(74) *Attorney, Agent, or Firm* — Muncy, Geissler, Olds & Lowe, P.C.

(57) ABSTRACT

Disclosed herein is a ceramic article with an increased surface roughness. The ceramic article includes a ceramic body having an engagement surface and a composite porous layer disposed on the engagement surface of the ceramic body. The composite porous layer is formed from a material including multiple first ceramic particles and multiple second ceramic particles. The sintering temperature of the first ceramic particle is lower than the melting temperature of the second ceramic particle, and at least some of the second ceramic particles are disperse within the composite porous layer whereby increasing the surface roughness of the ceramic article. Methods for manufacturing such ceramic article are also disclosed.

13 Claims, 8 Drawing Sheets

(51) Int. Cl.
  *B32B 5/02* (2006.01)
  *C04B 41/89* (2006.01)
  *C04B 41/00* (2006.01)
  *C04B 41/52* (2006.01)
  *A61C 5/08* (2006.01)
  *A61C 13/00* (2006.01)
  *C04B 41/45* (2006.01)
  *C04B 111/00* (2006.01)
  *C04B 38/00* (2006.01)

(52) U.S. Cl.
  CPC ........... *C04B 41/009* (2013.01); *C04B 41/4535* (2013.01); *C04B 41/4578* (2013.01); *C04B 41/4582* (2013.01); *C04B 41/52* (2013.01); *C04B 41/89* (2013.01); *C04B 38/0041* (2013.01); *C04B 2111/00836* (2013.01); *Y10T 428/24421* (2015.01)

(56) References Cited

U.S. PATENT DOCUMENTS

| | | | |
|---|---|---|---|
| 5,707,231 A | * | 1/1998 | Watt .................. A61C 7/141 433/8 |
| 2005/0136176 A1 | | 6/2005 | Rosenflanz et al. |
| 2007/0111165 A1 | * | 5/2007 | Wallick ................ A61C 8/0012 433/212.1 |
| 2007/0182042 A1 | | 8/2007 | Ikushima et al. |
| 2010/0130346 A1 | * | 5/2010 | Laine .................... B82Y 30/00 501/105 |
| 2011/0070452 A1 | | 3/2011 | Zhang et al. |
| 2013/0137064 A1 | | 5/2013 | Velamakanni et al. |

OTHER PUBLICATIONS

DE 102009051655 translation.*
Author Unknown, Dec. 10, 2013, American Elements: Yttrium Oxide, pp. 1-3, available at: 222.americanelements.com/yox.html.

* cited by examiner

CERAMIC ARTICLES WITH INCREASED SURFACE ROUGHNESS AND METHODS FOR MANUFACTURING THE SAME

CROSS-REFERENCE TO RELATED APPLICATION

This application is a divisional application of U.S. patent application Ser. No. 13/562,548, filed Jul. 31, 2012, which claims priority to Taiwan patent application No. 101105381, filed on Feb. 17, 2012, the entireties of which are incorporated herein by reference.

BACKGROUND OF THE INVENTION

1. Field of the Invention

The present disclosure relates to ceramic articles with increased surface roughness and methods for manufacturing the same. More particularly, the ceramic articles may be used as dental restorations, and the increased surface roughness thereof is advantageous in improving the bonding strength between the dental restoration and a resin adhesive for bonding the dental restoration to the abutment.

2. Description of Related Art

Oxide ceramics include aluminum oxide (alumina, $Al_2O_3$), zirconium oxide (zirconia, $ZrO_2$), silicon dioxide (silica, $SiO_2$), aluminum silicate (($AlO)_2SiO_3$), magnesium oxide (magnesia, MgO), and other metal oxide based materials. These ceramics have found applications in many fields due to their engineering properties (such as high hardness, fracture toughness, high melting point, and chemical inertness) and a wide range of electrical properties. For example, silicon dioxide-based ceramics (silicate ceramics) have long been used in dentistry because of their optical and aesthetic properties. Recently, high-strength ceramics such as zirconia and alumina ceramics have gained increasing popularity in utilization by clinicians and technicians due to the material's strength, and multitude of clinical indications and applications.

Nowadays, dental restorations are often bonded to the underlying abutment (such as natural tooth/teeth and dental implant(s)) with a resin adhesive. To improve the bonding strength between the dental restoration and the resin adhesive, the engagement surface (i.e., the surface configured to engage with an underlying abutment for retention thereto) of the dental restoration is often pretreated. Conventional surface treatments for dental restorations made of silicate ceramics (such as feldspar ceramics and glass ceramics) include micromechanical treatments, chemical treatments, and a combined treatment including both micromechanical and chemical treatments.

Micromechanical treatments such as acid etching and sandblasting create micro-cracks/pores on the treated surface which allow the resin adhesive to penetrate therethrough, and thereby improve the bonding strength of the dental restoration and the resin adhesive. Although micromechanical treatment is applicable for roughening silica-based ceramic, it has limited effect on the improvement of the surface roughness of high-strength ceramics because of the hardness and chemical inertness of these high-strength ceramics. Moreover, the micro-cracks/pores may result in the degradation of the flexural strength and fracture toughness of the dental restoration.

Chemical treatment involves the application of silane on the engagement surface. Silane, a molecule containing an organic group (e.g. vinyl, allyl, amino, etc.) and an inorganic group (e.g., methoxy, ethoxy, etc.), is widely used as a coupling agent. The inorganic group of the silane molecule hydrolyzes to produce silanol, which forms a metal hydroxide or siloxane bond with the inorganic material such as silicate ceramics. The organic group of the silane molecule reacts with the organic resin adhesive to produce a covalent bond. As a result, the organic resin adhesive and the inorganic ceramic are tightly bound. Yet, due to the chemical inertness of high-strength ceramics, the silane treatment has limited effects in improving the bonding strength between the resin adhesive and high-strength ceramics.

In sum, conventional surface treatments including acid etching, sandblasting, and silane coating are not suitable for improving the bonding strength between the high-strength ceramic and the resin adhesive. In view of the foregoing, there exists a need for a novel ceramic article, in particular a dental restoration, which has a satisfactory bonding strength with a resin adhesive, as well as a corresponding process for manufacturing it, in order to improve the clinical applicability and other utilities of such ceramic article.

SUMMARY

The following presents a simplified summary of the disclosure in order to provide a basic understanding for the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a ceramic article with an increased surface roughness. Generally, the ceramic article has a composite porous layer disposed on an engagement surface of a ceramic body. The micro- to nano-scale pores of the composite porous layer allow the penetration of resin adhesive thereby increasing the contact area of the ceramic/adhesive interface. Additionally, the plurality of microparticles dispersed within the composite layer, along with the pores, decrease the contact angle of the engagement surface, and thus increase the wettability of the engagement surface. Together, the increased contact area and wettability of the ceramic article would improve the bonding strength between the ceramic article and the resin adhesive. In one example, the present ceramic articles may be used as a component of a dental restoration; advantageously, the improved bonding strength may positively contribute to an increased service life of the dental restoration, as well as a better protection to the abutment.

According to one embodiment of the present disclosure, the ceramic article comprises a ceramic body and a composite porous layer. The ceramic body has an engagement surface configured to engage with an underlying structure (such as an abutment in the context of dentistry) for retention thereto. The composite porous layer disposed on the engagement surface is formed from a material comprising a plurality of first ceramic particles and a plurality of second ceramic particles. The sintering temperature of the first ceramic particle is lower than the melting temperature of the second ceramic particle, and at least some of the plurality of the second ceramic particles are dispersed within the composite porous layer whereby increasing the surface roughness of the engagement surface of the ceramic article. This should explain why it is necessary to have the sintering temperature of the first ceramic particle lower than the melting temperature of the second ceramic particle, as well as the fact that it allows some of the second ceramic particles to be redistributed in the composite porous layer without substantially fusing the second ceramic particles, and how this leads to increased surface roughness.

According to various embodiment of the present disclosure, the composite porous layer of the ceramic article has an average surface roughness (Ra) of at least about 0.5 µm; preferably, about 0.85-1.7 µm.

In certain embodiments, the ceramic body is made of a material comprising a metal oxide ceramic. Metal oxide ceramics include, but are not limited to, zirconium oxide and aluminum oxide.

According to some embodiments, the first ceramic particle is a glass ceramic such as an opaque dental ceramic. Alternatively or additionally, the second ceramic particle may have a Mohs hardness of at least 8.5 according to some embodiments of the present disclosure. For example, yttria-stabilized zirconia (YSZ) in which the yttria is present in an amount of about 0.5-35 mole percent may be used as the second ceramic particle. In one example, the second ceramic particle is 8 mol % yttria-stabilized zirconia (8YSZ).

Optionally, the composite porous layer may have a thickness of about 5-20 µm, and the second ceramic particle may have an average diameter of about 0.1-0.8 µm.

In another aspect, the present disclosure is directed to a method for manufacturing a ceramic article according to the above-mentioned aspect/embodiment(s) of the present disclosure. Generally, the method involves forming a composite porous layer on an engagement surface of a ceramic body. The resultant composite porous layer has pluralities of micro- to nano-scale pores and micro-particles dispersed within the composite porous layer, thereby increasing the surface roughness of the ceramic article. Accordingly, the bonding strength of the ceramic article with a resin adhesive that is used for fixing the ceramic article to an underlying structure (such as an abutment in the context of dentistry) is improved.

According to one embodiment of the present disclosure, the method comprises the steps as follows. In step (a), a first ceramic slurry comprising a plurality of first ceramic particles is coated on the engagement surface of the ceramic body. Then in step (b), the ceramic body from step (a) is sintered at a first sintering temperature to fuse the first ceramic particles whereby forming a ceramic basal layer on the engagement surface of the ceramic body. Afterwards, in step (c), a second ceramic slurry is coated on the ceramic basal layer, in which the second ceramic slurry comprises a plurality of first ceramic particles and a plurality of second ceramic particles in a weight ratio of about 9:1 to 1:1, in which the sintering temperature of the first ceramic particles is lower than the melting temperature of the second ceramic particles. In step (d), the ceramic body from step (c) is sintered at a second sintering temperature to fuse the ceramic basal layer and the first ceramic particles without substantially fusing the second ceramic particles whereby forming the composite porous layer on the engagement surface of the ceramic body.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

In accordance with common practice, the various described features/elements are not drawn to scale but instead are drawn to best illustrate specific features/elements relevant to the present invention. Also, like reference numerals and designations in the various drawings are used to indicate like elements/parts.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "dental restoration" means any restoration which may be used in the dental field. Illustrative examples of dental restoration include inlays, onlays, veneers, crowns, bridges, and posts.

The term "abutment" in accordance with the present disclosure refers to both natural tooth/teeth and dental implant(s) to which a dental restoration is to be attached or fixed.

"Sintering" in the sense of the present disclosure means densification of a powder, by heating the material without reaching the liquid state of the main constituents of the sintered material (solid state sintering). In other words, the sintering temperature is typically below the melting point of the main constituents.

One exemplary ceramic article according to the present disclosure and the method for manufacturing such ceramic article will be described hereinbelow with reference to FIG. 1 to facilitate understanding of the present disclosure.

Figure 1:
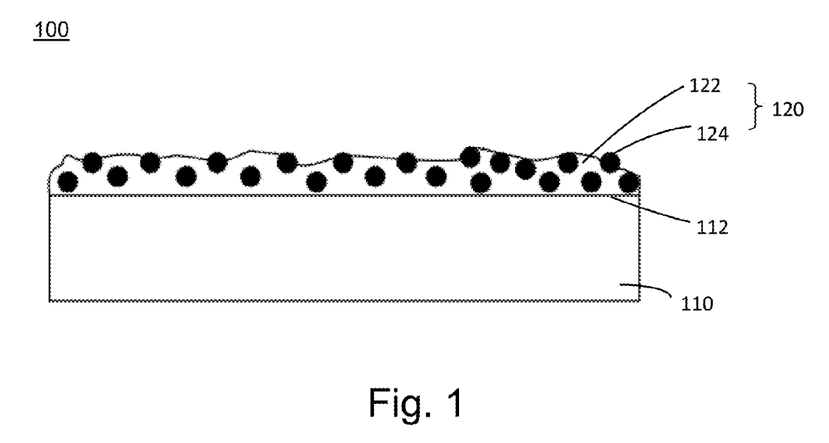
FIG. 1 is a schematic diagram illustrating a ceramic article according to one embodiment of the present disclosure.

The exemplary ceramic article 100 as illustrated in FIG. 1 comprises a ceramic body 110 and a composite porous layer 120 disposed on an engagement surface 112 of the ceramic body 110, and the ceramic article 100 is manufactured by a method comprising the following steps.

In step (a), a first ceramic slurry (not shown) is coated on the engagement surface 112 of the ceramic body 110. Generally, the first ceramic slurry is prepared by mixing a first ceramic powder with a modeling liquid. In one example, the modeling liquid may be distilled water. Alternatively, the modeling liquid may be any commercially available modeling liquids that are specifically designed to create a homogeneous mixture. The first ceramic slurry is then applied onto the engagement surface 112 with the aid of a suitable means such as a brush or other applicators.

According to various embodiments of the present disclosure, the ceramic body 110 may be made of a material comprising a metal oxide ceramic, such as zirconium oxide and aluminum oxide. In practice, the ceramic body 110 may optionally be pre-fabricated ceramics in different shapes, sizes, and even colors that suit the specific application of the final product. Additionally or alternatively, the ceramic body 110 or the ceramic article 100 may be post-processed to give its final shape, size, and/or color to the product. In certain working examples according to the present disclosure, a pre-sintered 5 mol % yttria-stabilized zirconia substrate such as 3M-ESPE LAVA™ Frame commercially available by 3M-ESPE (St Paul, Minn., USA), was used as the ceramic body 110.

In certain embodiments, the first ceramic particle is a glass ceramic such as an opaque dental ceramic. For example, the VITA VM®9 EFFECT LINER (3M-ESPE, St Paul, Minn., USA) was used as the first ceramic particle.

Then in step (b), the ceramic body 110 from step (a) is sintered at a first sintering temperature so that the first ceramic particles of the first ceramic powder are fused (adhered) together to form a ceramic basal layer (not shown) on the engagement surface 112 of the ceramic body 110.

The sintering process is generally carried out in commercially available sintering furnaces (such as the VITA VACUMAT® 40T (3M Taiwan Ltd., Taiwan) furnace used in the present disclosure) or other equivalent apparatus. The choice of the first sintering temperature depends on the composition of the first ceramic particles. For most commercially available dental opaques, the sintering temperature is about 850-1000° C., and the sintering temperature for the VITA VM®9 EFFECT LINER used in the working examples is about 900-950° C. The duration of the sintering process varies with factors such as the species of the first ceramic particles, and the amount of the slurry coated on the ceramic body 110. Further, the duration may be determined by persons having ordinary skills in the art based on their experiences or protocols provided by the manufacturers of the ceramic materials or sintering furnaces. Optionally, the first sintering process is carried out in multiple stages having various temperatures and durations so as to achieve a more desirable sintering effect.

After the formation of the ceramic basal layer (not shown), the present method proceeds to step (c) in which a second ceramic slurry is coated on the ceramic basal layer of the ceramic body 110. Similarly to step (a), the second slurry is coated onto the ceramic basal layer with the aid of a brush or other suitable applicators.

The second ceramic slurry is formed from a mixture comprising the first ceramic powder and a second ceramic powder in a weight ratio of about 9:1 to 1:1; preferably, about 5:1 to 1:1. According to principles and spirits of the present disclosure, the second ceramic powder shall have a melting temperature which is greater than the sintering temperature of the first ceramic powder such that the ceramic particles of the second ceramic powder would not be fused under a sintering condition that is sufficient to fuse the first ceramic particles. Preferably and optionally, the melting temperature of the first ceramic particle is lower than the melting temperature of the second ceramic particle.

In optional embodiments, the second ceramic particles have an average diameter of about 0.1-0.8 µm; preferably, about 0.1-0.2 µm. For example, the average diameter may be about 0.1, 0.15, 0.2, 0.25, 0.3, 0.35, 0.4, 0.45, 0.5, 0.55, 0.6, 0.65, 0.7, 0.75, or 0.8 µm. Results from working examples as summarized hereinbelow suggest that a composite porous layer having second ceramic particles with a diameter exceeding 0.8 µm would not result in a satisfactory improvement regarding the bonding strength, albeit increases surface roughness was observed.

Still optionally, the second ceramic particle may have a Mohs hardness of at least 8.5 according to some embodiments of the present disclosure. Moreover, for ceramic articles that are intended to use in biomedical fields such as orthopedics and dentistry, the second ceramic particles are preferably biocompatible. For example, yttria-stabilized zirconia (YSZ) in which the yttria is present in an amount of about 0.5-35 mole percent may be used as the second ceramic particle. In one example, the second ceramic particle is 8 mol % yttria-stabilized zirconia (8YSZ), which has a melting temperature of about 2680° C. and a Mohs hardness of about 8.5.

The two ceramic powders may come in a pre-mixed or mixed-on-site form. Optionally, the first and second ceramic powders are ball-milled to provide a mixture with a more satisfactory homogeneity. The mixture comprising the first and second ceramic powders are mixed with a suitable modeling liquid to give the second ceramic slurry. The modeling liquid used in step (c) may be same as or different from the modeling liquid used in step (a); however, in preferable embodiments, they are the same.

Then, in step (d), the ceramic body 110 from step (c) is sintered at a second sintering temperature so as to fuse the ceramic basal layer with the first ceramic particles without substantially fusing the second ceramic particles and whereby forming the composite porous layer 120 on the engagement surface 112 of the ceramic body 110.

As could be appreciated, it is vital to use a second sintering temperature that is lower than the sintering temperature (and thus the melting temperature) of the second ceramic particles, so as to prevent fusion of the second ceramic particles with the ceramic basal layer. During the second sintering process, the sintered, first ceramic material 122 (including the ceramic basal layer as well as the first ceramic particles in the second ceramic slurry) would flow across the engagement surface 112 of the ceramic body 110. However, the presence of the un-sintered, second ceramic particles 124 would impede the continuous flow of the first ceramic material. Therefore, multiple pores (voids) are formed on the surface of the composite porous layer 120, and some of the second ceramic particles 124 are dispersed within the composite porous layer 120. The pores allow the penetration of the resin adhesive (not shown) that is used to fix the ceramic article 100 to an underlying structure (not shown), thereby increasing the bonding strength between the ceramic article 100 and the resin adhesive. Moreover, the pores and second ceramic particles 124 on the surface contribute to the increased surface roughness of the ceramic article 100, and the increased contact area resulting from the increased surface roughness would also improve the bonding strength between the ceramic article 100 and the resin adhesive.

In certain embodiments of the present disclosure, the composite porous layer 120 has a thickness of about 5-20 µm; preferably, 10-20 µm. In some embodiments, the average surface roughness (Ra) of the composite porous layer 120 is at least 0.5 µm; preferably, about 0.85-1.7 µm.

As described hereinabove, the present method is advantageous in that he bonding strength between the ceramic article 100 and the adhesive resin is improved, and thereby enhances the applicability of such ceramic article in various fields. As a result, ceramic article thus produced may be used in conjunction with other metal components to provide a product with sufficient bonding strength. For example, a conventional Maryland bridge consists of at least one artificial ceramic tooth and two metal wings (retainers) attached to the sides of the artificial tooth. The metal wings are prepared in a way that each possesses a porous surface so that it can receive a bonding agent, and then the wings are bonded to the back sides of the teeth (abutments) on either side of the missing tooth.

Figure 2:
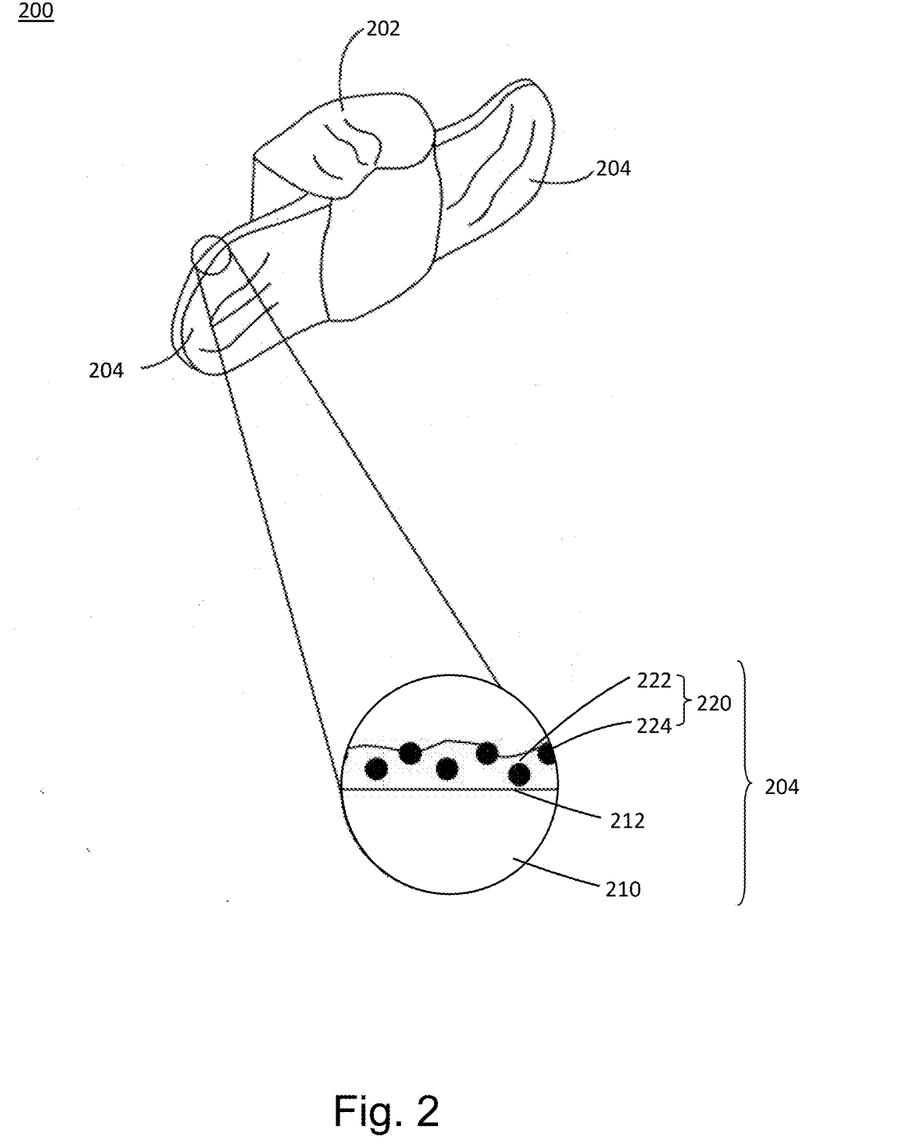
FIG. 2 is a schematic diagram illustrating an all-ceramic Maryland bridge and a sectional, partial enlargement view thereof, according to one embodiment of the present disclosure.

However, the present method opens a way for the application of all-ceramic materials made of high-strength ceramics. In one embodiment, the ceramic article may be manufactured as an all-ceramic Maryland bridge 200 as illustrated in FIG. 2. The all-ceramic Maryland bridge 200 comprises an artificial tooth 202 and two wings (retainers) 204. In this case, the artificial tooth 202 and the two wings (retainers) 204 may be integrally formed from a high-strength ceramic material 210 such as LAVA™ FRAME, and then the engagement surfaces 212 of the wings 204 are treated in accordance with the present method thereby forming a composite porous layer 220 on the engagement surfaces 212. The composite porous layer 220 is formed from a material comprising a first ceramic material 222 (e.g., VITA VM®9 EFFECT LINER), and a plurality of second ceramic particles 224 (e.g., 8-YSZ). Together, the pores formed on the surface of the composite porous layer 220 and the second ceramic particles 224 dispersed within the composite porous layer 220 may increase the contact area of the composite porous layer 220. In this way, the bonding strength between the wings 204 of the all-ceramic Maryland bridge 200 and the adhesive resin is enhanced.

In this embodiment, the thickness of the composite porous layer 220 is about 10-20 µm, and therefore, the formation of the composite porous layer 220 on the wings 204 would not substantially increase the occlusal height of the Maryland bridge 200. Preferably, the second ceramic particles 224 may have an average diameter of about 0.1-0.8 µm; more favorably, 0.1-0.2 µm.

Figure 3:
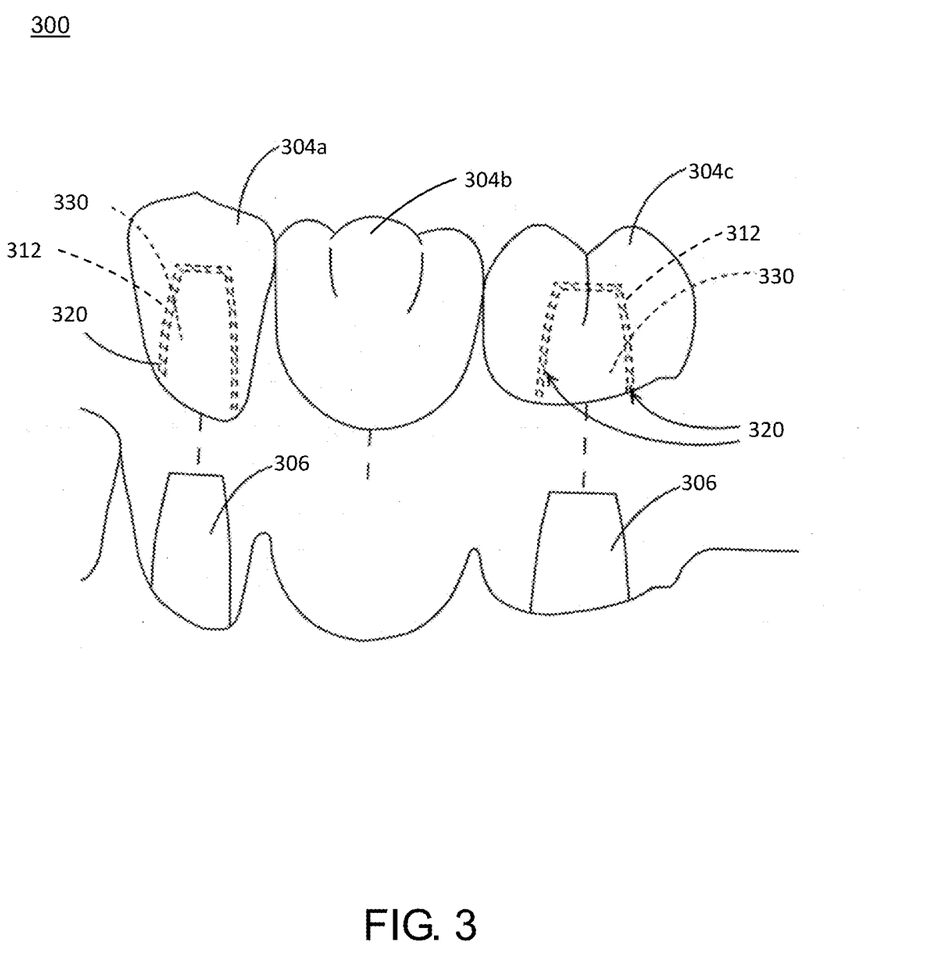
FIG. 3 is a schematic diagram illustrating an all-ceramic 3-unit bridge according to one embodiment of the present disclosure.

In an alternative embodiment, the ceramic article may be manufactured as an all-ceramic three-unit bridge 300 as illustrated in FIG. 3. The all-ceramic 3-unit bridge 300 comprises three artificial teeth 304a-c joined alongside each other in a row, the two artificial teeth 304a and 304c on each side are intended to be attached over two abutments 306 (such as the natural tooth, dental post, or other dental implant). The artificial teeth 304a and 304c are shaped to have an insertion recess 330 therein for fittingly engaging with the abutments 306. Similarly, the three-unit bridge 300 may be integrally made from a high-strength ceramic material such as LAVA™ FRAME. Thereafter, the engagement surface 312 defining the insertion recess 330 is treated in accordance with the method described herein to form a composite porous layer 320 thereon. Although not explicitly illustrated in FIG. 3, the composite porous layer 320, like the composite porous layer 220, is formed from a material comprising a first ceramic material (e.g., VITA VM®9 EFFECT LINER), and pluralities of second ceramic particles (e.g., 8-YSZ). Therefore, the bonding strength between the all-ceramic three-unit bridge 300 and the resin adhesive is improved.

The following examples and comparative examples are provided to elucidate certain aspects of the present invention and to aid those of skilled in the art in practicing this invention. The scope of the invention is in no way limited to the examples provided. Without further elaboration, it is believed that one skilled in the art can utilize the present invention to its fullest extent based on the description herein.

Example I

Preparation of Ceramic Sample

The green blank of pre-sintered zirconia (3M-ESPE LAVA™ Frame, 3M-ESPE, St Paul, Minn., USA) was dry-cut by a low-speed cutting machine into a size of 20×15×4 mm$^3$ so as to give a sample having a size of 18×13×3 mm$^3$ after firing. The sample was sanded with waterproof sand paper (grit #100, 200, 400, 800, 1000, 1200, 1500, and 2000) and polished with polishing fluid containing $Al_2O_3$ powders (1.0 µm and 0.3 µm) thereby giving the sample an average surface roughness of about 0.02 µm. Afterwards, the sample was cleaned with 95% alcohol under ultrasonic vibration and then oven-dried.

Example II

Surface treatment of Ceramic Sample

In the working examples, the ceramic samples were treated in accordance with methods according to embodiments of the present disclosure.

In particular, to form a ceramic basal layer on the sample, VITA VM®9 EFFECT LINER (3M-ESPE, St Paul, Minn., USA) was mixed with VITA VM® modeling liquid to give the first slurry. A thin, even layer of the first slurry was applied to a surface of the sample using a brush, and the sample was left standing in the air for about 10 minutes. Then, the sample was sintered in VITA VACUMAT® 40T furnace with the sintering process as follows. The starting temperature of about 575° C. is maintained for about 6 minutes. Thereafter, the furnace was heated to the sintering temperature of about 930° C. at a rate of about 55° C./min (approximate heat-up time: 7.5 minutes), and then the furnace was vacuumed for about 7.5 minutes. Upon finishing sintering the ceramic basal layer, the furnace was cooled down to about 540° C. and lasted for about 1 minute.

The second slurry comprising two different ceramic particles was prepared as follows. The VITA VM®9 EFFECT LINER and the 8YSZ powder (diameter of 0.15 μm or 1 μm) were mixed in the amount summarized in Table 1. The mixture (about 0.4 g) was then mixed with a suitable amount of deionized water and zirconia balls (as milling medium), and then subjected to wet-milling for about 24 hours (rpm: 360). The mixture was then dried and grounded to give a composite powder. The composite powder was mixed with mixed with VITA VM® modeling liquid to give the second slurry. A thin, even layer of the second slurry was applied over the ceramic basal layer with a brush, and the sample was stood in the air for about 10 minutes. Then, the sample was sintered in VITA VACUMAT® 40T furnace with a second sintering process same as the sintering process for forming the ceramic basal layer. During this second sintering process, the ceramic basal layer and the VITA VM®9 EFFECT LINER within the second slurry would be fused (sintered), while the 8YSZ particles would not be fused due to their high melting temperature, and thereby formed a composite porous layer over the surface of the ceramic article. After the sintering of the composite porous layer, the furnace was cooled down to about 540° C. and lasted for about 1 minute. These ceramic samples are designated as VZ-A1 to VZ-A5 (for composite porous layer having 0.15 μm-8YSZ) and VZ-B1 to VZ-B5 (for composite porous layer having 1 μm-8YSZ) hereinafter.

Example III

Comparative Examples

Comparative samples in which the ceramic samples were treated with conventional methods or coated with other composite powders were also prepared. 6 samples were used in each of the comparative examples.

For acid etching, samples were immersed in various etching solution for a time period specified in Table 2. The acid etching processes include HF etching (9.5% HF), hot etching (800 ml of methanol, 200 ml of HCl, and 2 g of $FeCl_3$ at 80° C.), and chemical etching (3 or 10 drops of HF, 30 ml of $HNO_3$, and 60 ml of deionized water). The acid etching was carried out in the fume hood. Upon the completion of the etching treatment, the sample was washed with water for about 1 minute, and cleaned with 95% alcohol under ultrasonic vibration for about 5 minutes and then oven-dried. These comparative ceramic samples are designated as CE-1 to CE-9 hereinafter.

$Al_2O_3$ (average diameter: 50 μm) sandblasting was performed manually with Micro bar at a distance of about 10 cm for about 20 seconds. The treated sample was then cleaned with 95% alcohol under ultrasonic vibration and then oven-dried. These comparative ceramic samples are designated as CE-10 hereinafter.

For comparative composite coating, PMMA (poly(methyl methacrylate)) particles (spherical shape or elliptic shape) was used in place of 8YSZ particles used in Example II, the weight ratios between the VITA VM®9 EFFECT LINER and PMMA particles are summarized in Table 3. The melting temperature of PMMA is about 160° C., which is lower than the melting temperature of the first ceramic material (VITA VM®9 EFFECT LINER). The composite powder containing the VITA VM®9 EFFECT LINER and PMMA was applied on a surface of the ceramic sample and sintered in accordance with steps set forth in Example II. As could be appreciated, these PMMA particles would be evaporated during the second sintering process due to its low boiling point thereby leaving voids (pores) in the resultant layer. These comparative ceramic samples are designated as CP-A1 to CP-A5 (for composite porous layer having spherical PMMA) and CP-B1 to CP-B5 (for composite porous layer having elliptic PMMA) hereinafter.

Example IV

Bonding Between Sample and Resin Adhesive

Three resin adhesives (PANAVIA™, RELYX™ U100, and RELYX™ ARC) were employed to investigate the bonding strength between the sample and the resin adhesive. The resin adhesive was sandwiched between two sample sheets with the surfaces that are treated by the present method or comparative method facing each other, and the resulting article was fixed with a jaw. Excess amount of resin adhesive was removed from the bonded article by brush, and then each lateral side of the bonded article was irradiated by UV light for about 20 seconds to allow for curing of the peripheral resin adhesive. The article was then stood in the air for approximately one day to allow for curing of the internal portion of the resin adhesive.

Example V

Property Analysis (I) Measurement of Average Surface Roughness

The average surface roughness (Ra) of each sample was conducted by alpha-step surface profiler (KOSAKA SEF-3500; Mode: ISO 97 (Roughness); Scan distance: 2 mm; Scan rate: 0.2 mm/s; Z-axis: 2000X).

(II) Microscopic Observation

Field emission scanning electron microscope (HITACHI S-4700) was used to investigate the surface morphology and cross-sectional morphology of the sample. In some examples, the bonded articles from Example IV were immersed in deionized water at 37° C. for about 1 day and 30 days, respectively, before the microscopic observation. This water storage treatment was intended to simulate the oral environment in which the ceramic article may be used.

(III) Micro-Tensile Bonding Strength Test

After water storage, the bonded articles from Example V(II) were prepared into tensile test bar (size: $1\times1\times6\,mm^3$) by a low-speed cutting machine, and the average bonding strength thereof was measured by Micro tensile tester (BISCO).

Results

Weight ratios between the first ceramic powder (VITA VM° 9 EFFECT LINER) and the second ceramic powder (8YSZ) in the working examples are summarized in Table 1, together with the average surface roughness (Ra) of ceramic samples coated with the composite porous layer prepared in Example II. Also, the average surface roughness (Ra) of comparative ceramic samples from the comparative examples from Example III and the respective treatment thereof are summarized in Table 2. The results are shown as means±SE of 8 samples for each experimental group.

TABLE 1

Surface roughness of ceramic articles according to present disclosure.

| Example | Liner/8YSZ Weight Ratio | Ra (μm) |
| --- | --- | --- |
| VZ-A1 | 9:1 | 0.94 ± 0.10 |
| VZ-A2 | 8:2 | 1.45 ± 0.25 |
| VZ-A3 | 7:3 | 1.68 ± 0.16 |
| VZ-A4 | 6:4 | 0.85 ± 0.21 |
| VZ-A5 | 5:5 | 1.65 ± 0.21 |
| VZ-B1 | 9:1 | 1.00 ± 0.07 |
| VZ-B2 | 8:2 | 1.04 ± 0.16 |
| VZ-B3 | 7:3 | 0.98 ± 0.21 |
| VZ-B4 | 6:4 | 1.80 ± 0.09 |
| VZ-B5 | 5:5 | 1.68 ± 0.16 |

TABLE 2

Surface roughness of ceramic articles according to comparative examples.

| Example | Treatment | Ra (μm) |
| --- | --- | --- |
| CE-1 | HF etching; 30 sec. | 0.02 ± 0.007 |
| CE-2 | HF etching; 60 sec. | 0.03 ± 0.007 |
| CE-3 | HF etching; 90 sec. | 0.03 ± 0.009 |
| CE-4 | Hot etching; 1.5 hrs. | 0.15 ± 0.027 |
| CE-5 | Hot etching; 3 hrs. | 0.13 ± 0.022 |
| CE-6 | Chemical etching; 3 drops, 1.5 hrs. | 0.04 ± 0.004 |
| CE-7 | Chemical etching; 3 drops, 3 hrs. | 0.04 ± 0.004 |
| CE-8 | Chemical etching; 10 drops, 1.5 hrs. | 0.03 ± 0.007 |
| CE-9 | Chemical etching; 10 drops, 3 hrs. | 0.05 ± 0.006 |
| CE-10 | $Al_2O_3$ sandblasting | 0.30 ± 0.030 |
| CP-A1 | Liner:spherical PMMA = 9:1 | 1.78 ± 0.19 |
| CP-A2 | Liner:spherical PMMA = 8:2 | 0.89 ± 0.08 |
| CP-A3 | Liner:spherical PMMA = 7:3 | 0.91 ± 0.14 |
| CP-A4 | Liner:spherical PMMA = 6:4 | 0.86 ± 0.08 |
| CP-A5 | Liner:spherical PMMA = 5:5 | 1.51 ± 0.13 |
| CP-B1 | Liner:elliptic PMMA = 9:1 | 1.20 ± 0.08 |
| CP-B2 | Liner:elliptic PMMA = 8:2 | 1.04 ± 0.16 |
| CP-B3 | Liner:elliptic PMMA = 7:3 | 1.42 ± 0.16 |
| CP-B4 | Liner:elliptic PMMA = 6:4 | 1.43 ± 0.16 |
| CP-B5 | Liner:elliptic PMMA = 5:5 | 1.50 ± 0.13 |

The data summarized in Table 1 indicated that the surface roughness of ceramic samples according to embodiments of the present disclosure was increased from about 0.02 μm (the untreated sample from Example I) to at least 0.8 μm. By contrast, the ceramic samples treated by conventional methods such as acid etching and sandblasting could not substantially increase the surface roughness of the ceramic samples. Specifically, the surface roughness of ceramic samples treated by HF etching was only about 0.02-0.03 μm, which was similar to that of the untreated sample from Example I. Chemical etching slightly increased the surface roughness from about 0.02 μm to about 0.03 to 0.05 μm. Hot etching was the most effective among the acid etching approaches which increased the surface roughness from about 0.02 μm to about 0.15 μm. Sandblasting was more effective than acid etching; however the surface roughness of sandblasted ceramic samples (0.3 μm) was still unsatisfactory and was much lower than the surface roughness of the ceramic samples according to working examples of the present disclosure.

As to comparative examples CP-A1 to CP-A5 and CP-B1 to CP-B5, the porous layer formed on the surface of the ceramic sample consists primarily of single component (i.e., the VITA VM®9 EFFECT LINER) because the PMMA particles were evaporated during the sintering process. Although this approach resulted in an increase of surface roughness of the ceramic sample (at least 0.8 μm) which was commensurate with the working examples provided herein, however, further investigation revealed that this single-component porous layer was not effective in improving the bonding strength of the ceramic samples.

Figure 4:
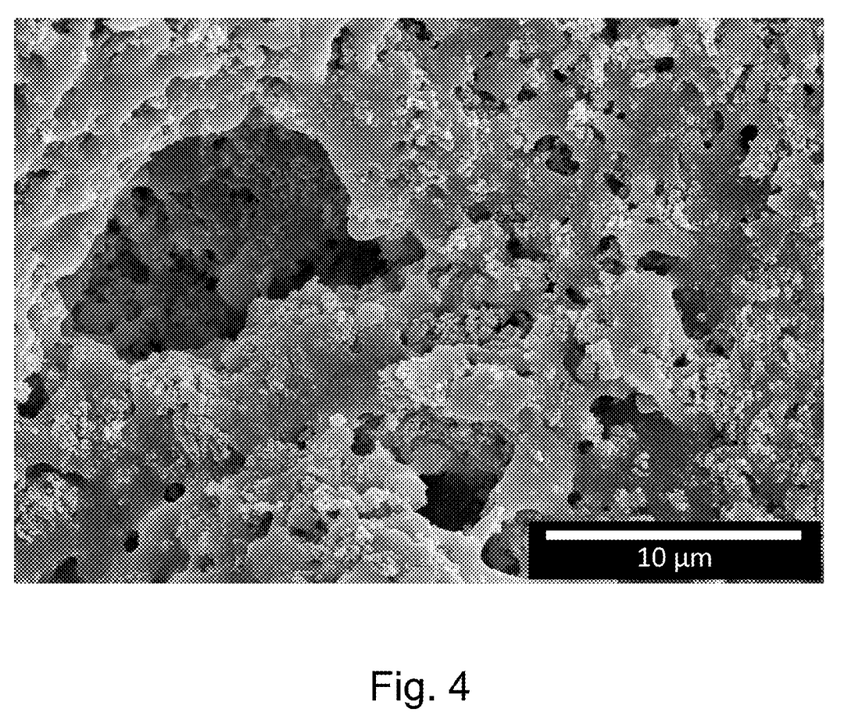
FIG. 4 is a scanning electronic microscopic (SEM) photograph illustrating the surface of a VZ-A5 ceramic sample according to one example of the present disclosure.

FIG. 4 is a microscopic photograph illustrating the surface morphology of the composite porous layer of the ceramic sample of example VZ-A5 (hereinafter, VZ-A5 sample). As could be seen in FIG. 4, there are pluralities of white particles dispersed within the composite porous layer. Analysis with energy dispersive spectrometer (EDS) confirmed that these white particles were 8YSZ particles.

Figure 5:
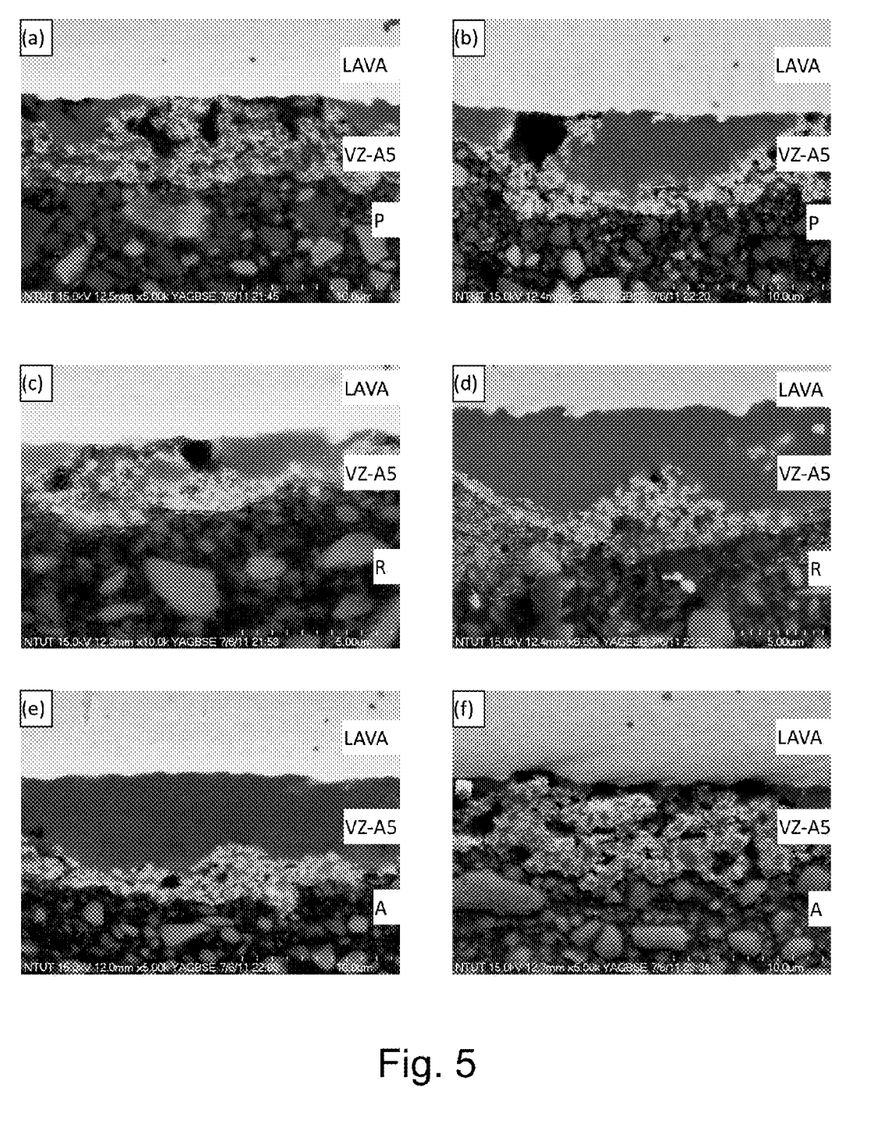
FIG. 5 provides scanning electronic microscopic (SEM) photographs respectively illustrating the cross-sectional views of ceramic articles after water storage for 1 day or 30 days, in which the ceramic articles are VZ-A5 samples bonded with various resin adhesive according to one example of the present disclosure.
Figure 6:
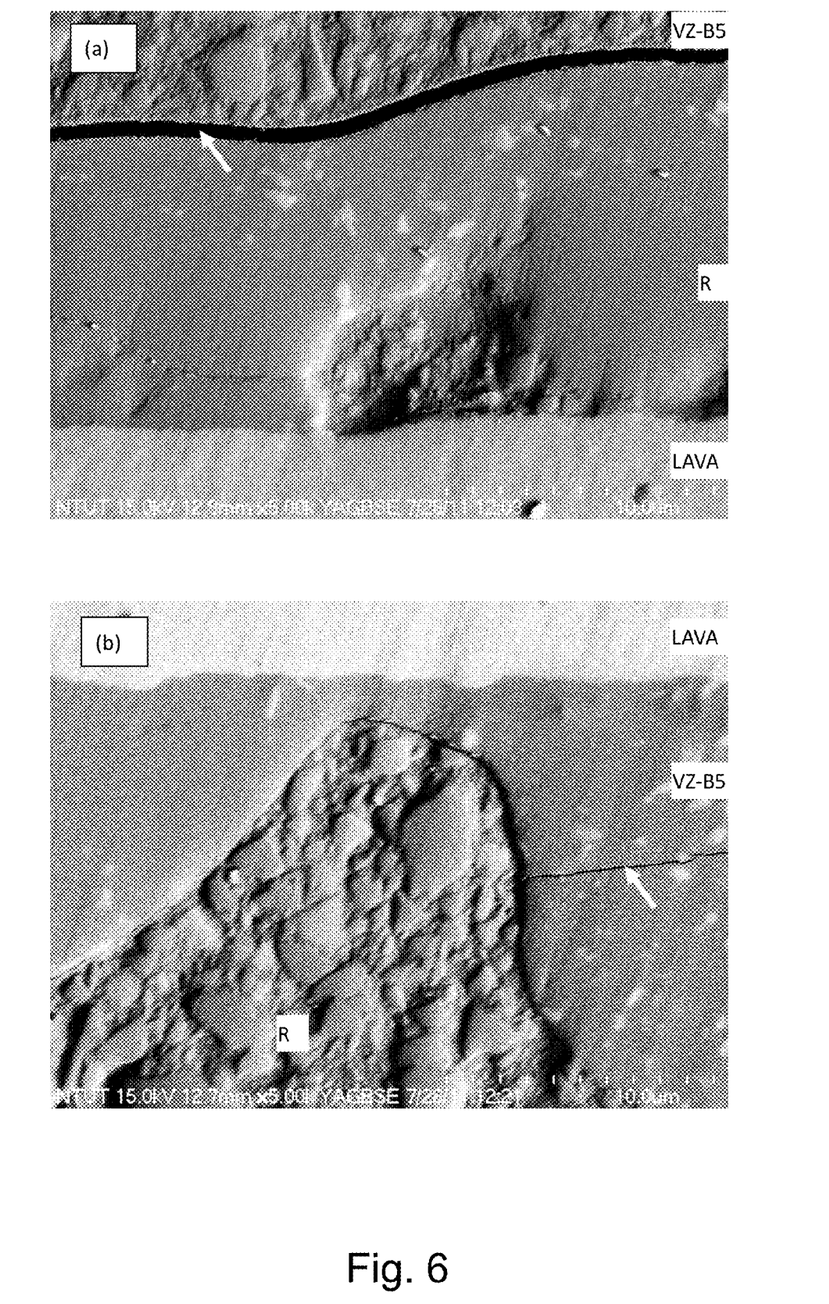
FIG. 6 provides scanning electronic microscopic (SEM) photographs respectively illustrating the cross-sectional views of ceramic articles after water storage for 1 day or 30 days, in which the ceramic articles are VZ-B5 samples bonded with RELYX™ U100 resin adhesive according to one comparative example of the present disclosure.
Figure 7:
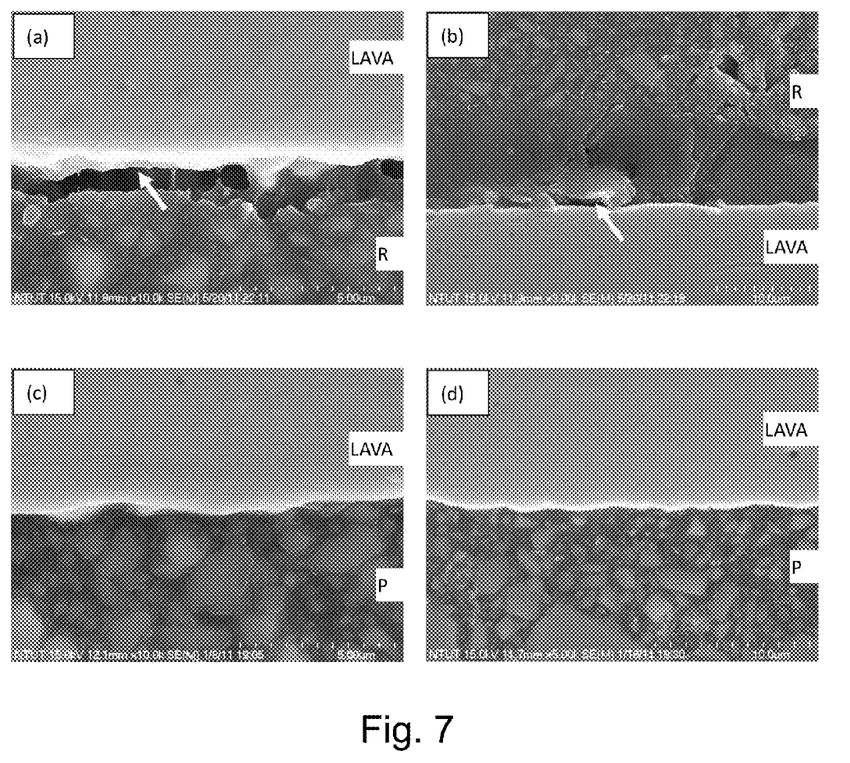
FIG. 7 provides scanning electronic microscopic (SEM) photographs respectively illustrating the cross-sectional views of ceramic articles after water storage for 1 day or 30 days, in which the ceramic articles are CE-5 samples bonded with RELYX™ U100 resin adhesive and CE-10 samples bonded with PANAVIA™ resin adhesive according to one example of the present disclosure.
Figure 8:
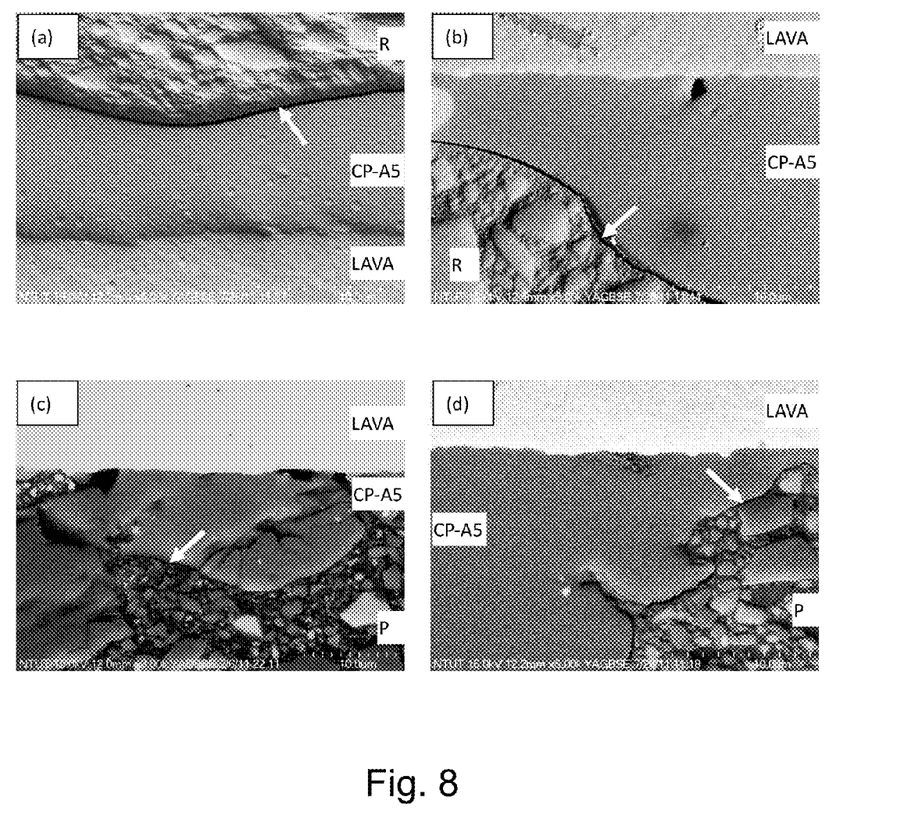
FIG. 8 provides scanning electronic microscopic (SEM) photographs respectively illustrating the cross-sectional views of ceramic articles after water storage for 1 day or 30 days, in which the ceramic articles are CP-A5 samples bonded with RELYX™ U100 resin adhesive or PANAVIA™ resin adhesive according to one example of the present disclosure.

The ceramic samples were bonded with various resin adhesives (PANAVIA™, RELYX™ U100, or RELYX™ ARC) and underwent water storage (WS) for 1 day or 30 days; the microscopic photographs illustrating the cross-sectional structures of these bonded ceramic samples were provided in FIG. 5 (VZ-A5 sample), FIG. 6 (VZ-B5 sample), and FIGS. 7-8 (comparative samples).

Test bars were prepared from the ceramic/resin bonded articles to elucidate the bonding strength between the ceramic and resin adhesive; the results are summarized in Table 3 and shown as means±SE of 8 samples for each experimental group. Most bonded articles formed from comparative ceramic samples broke during the preparation of the test bar; these bonded articles are designated as F (failure) in Table 3.

TABLE 3

Bonding strength

| | | Bonding strength (MPa) | |
| --- | --- | --- | --- |
| Sample | Resin Adhesive | 1 Day WS | 30 Days WS |
| VZ-A5 | PANAVIA | 21.34 ± 6.67 | 25.15 ± 4.24 |
| | RELYX U100 | 34.35 ± 3.26 | 36.65 ± 3.71 |
| | RELYX ARC | 18.58 ± 3.12 | 30.46 ± 8.42 |
| VZ-B5 | PANAVIA | F | F |
| | RELYX U100 | F | F |
| | RELYX ARC | F | F |
| CE-5 | PANAVIA | F | F |
| | RELYX U100 | F | F |
| | RELYX ARC | F | F |
| CE-10 | PANAVIA | 35.60 ± 10.77 | F |
| | RELYX U100 | F | 23.23 ± 1.83 |
| | RELYX ARC | F | F |
| CP-A5 | PANAVIA | F | F |
| | RELYX U100 | F | F |
| | RELYX ARC | F | F |
| CP-B5 | PANAVIA | F | F |
| | RELYX U100 | F | F |
| | RELYX ARC | F | F |

As could be seen in FIG. 5, after water storage for one day, no crack was observed in the VZ-A5 sample bonded with PANAVIA™ (denoted as "P" in all figures) (FIG. 5 (a)), RELYX™ U100 (denoted as "R" in all figures) FIG. 5 (c)), or RELYX™ ARC (denoted as "A" in all figures) FIG. 5 (e)). Moreover, even after water storage for 30 days, the bonding between the VZ-A5 sample and PANAVIA™ (FIG. 5 (b)), RELYX™ U100 (FIG. 5 (d)), or RELYX™ ARC (FIG. 5 (f)) was still tight, and no crack was seen. These observations were consistent with the results of the micro-tensile bonding strength test. The VZ-A5/resin bonded articles exhibited a bonding strength of at least 20 MPa. In particular, the VZ-A5/ RELYX™ U100 bonded article exhibited a bonding strength of at least 35 MPa, which was suitable for clinical application. Moreover, in each group, the bonding strength after 30 days of water storage was increased as compared with the bonding strength after 1 day of water storage. This was probably due to the self-polymerization of the resin adhesive during the 30 days of water storage.

Ceramic sample from example VZ-B5 (VZ-B5 sample, hereinbelow) also exhibited increased surface roughness, in comparison with untreated ceramic sample. However, cracks were observed in the VZ-B5/resin bonded articles. For example, cracks (indicated by arrow head) were observed in the VZ-B5/RELYX™ U100 bonded article, after water storage for one day (FIG. 6(a)) and 30 days (FIG. 6(b)). All VZ-B5/resin bonded articles broke during the preparation of the test bar, which coincided with the above-mentioned findings in microscopic observation.

All of the bonded articles formed from hot etched ceramic samples (CE-5) failed to give any test bar. For example, ceramic sample from comparative example CE-5 (CE-5 sample, hereinbelow) was bonded with RELYX™ U100 resin adhesive, and cracks (indicated by arrow head) were found after water storage for one day (FIG. 7(a)) and 30 days (FIG. 7(b)).

The sandblasted ceramic sample from example CE-10 (CE-10 sample, hereinbelow) was bonded with PANAVIA™ resin adhesive, and no crack was observed after water storage for one day (FIG. 7(c)) and 30 days (FIG. 7(d)). The bonding strength of the CE-10/PANAVIA bonded article was 35.60 MPa; however, it was noted that the standard error of this group was quite large (±10.77), which reflected the finding that the bonding strengths of the samples in this group notably varied from one another. Also, the CE-10/PANAVIA bonded articles, after 30 days of water storage, failed to give the test bars; suggesting that the long-term water storage may deteriorate the bonding between the CE-10 sample and the PANAVIA resin. Regarding the CE-10/RELYX™ U100 bonded articles, test bars were obtained from groups subjected to 30 days of water storage but not from groups subjected to 1 day of water storage.

Ceramic samples from comparative examples CP-A5 and CP-B5 (hereinbelow, CP-A5 sample and CP-B5 sample, respectively), like VZ-A5 samples, also exhibited increased surface roughness, in comparison with untreated ceramic sample. However, cracks were observed in bonded articles formed from CP-A5 and CP-B5 samples. For example, cracks (indicated by arrow head) were observed in the CP-A5/RE-LYX™ U100 bonded article, after water storage for one day (FIG. 8(a)) and 30 days (FIG. 8(b)), as well as in the CP-A5/PANAVIA bonded article, after water storage for one day (FIG. 8(c)) and 30 days (FIG. 8(d)). All VZ-B5/resin bonded articles broke during the preparation of the test bar, which coincided with the above-mentioned findings in microscopic observation.

In view of the foregoing results, it is concluded that the coating of a composite porous layer comprising 0.15 µm of 8YSZ particles (VZ-A5 sample) is effective in increasing both the surface roughness of the ceramic article and the bonding strength between the ceramic article and the resin adhesive. By contrast, the coating of a composite porous layer comprising 1 µm of 8YSZ particles (VZ-B5 sample) or single-component porous layer comprising spherical (CP-A5) or elliptic (CP-B5) PMMA particles fails to increase the bonding strength albeit the increase in surface roughness is observed. Other conventional surface treatments including acid etching and sandblasting fail to increase either the surface roughness or the bonding strength to an extent sufficient for clinical application.

In sum, embodiments of the present disclosure provide an easy-to-manufacture ceramic article with an increased surface roughness and thus an improved bonding strength, as well as a corresponding method for manufacturing it. Accordingly, the present disclosure facilitates the clinical application of all-ceramic material made of high-strength ceramics such as zirconium oxide and aluminum oxide. Particularly, the present ceramic article provides sufficient wettability to allow the penetration of resin adhesive into the pores of the composite porous layer, thereby increasing the bonding strength. Moreover, the composite porous layer itself exhibits sufficient bonding strength with the ceramic body on which it is coated so that the composite porous layer would not break away from the ceramic body. Also, the present composite porous layer is thin enough such that it would not substantially increase the occlusal height after being inserted.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for forming a composite porous layer at an engagement surface of a ceramic body, comprising the steps of:
   (a) coating a first ceramic slurry on the engagement surface of the ceramic body, wherein the first ceramic slurry comprises a plurality of a first type of ceramic particles;
   (b) sintering the ceramic body of the step (a) at a first melting temperature to fuse the plurality of the first type of ceramic particles such that a ceramic basal layer is formed on the engagement surface of the ceramic body;
   (c) coating a second ceramic slurry on the ceramic basal layer, wherein the second ceramic slurry comprises a plurality of the first type of ceramic particles and a plurality of a second type of ceramic particles in a weight ratio of 9:1 to 1:1, wherein each of the plurality of the second type of ceramic particles is 8 mol % yttria-stabilized zirconia (8YSZ), and the sintering temperature of the first type of ceramic particles is lower than the melting temperature of the second type of ceramic particles; and
   (d) sintering the ceramic body of the step (c) at a second melting temperature which is no less than the sintering temperature of the first type of ceramic particles but less than the melting temperature of the second type of ceramic particles such that the ceramic basal layer and the plurality of the first type of ceramic particles are fused while at least some of the plurality of the second type of ceramic particles remain unfused, whereby forming a composite porous layer having the unfused second type of ceramic particles dispersed therewithin and having an average surface roughness (Ra) of about 0.85-1.7 µm, wherein the ceramic body is a dental restoration, and the composite porous layer at the engagement surface is configured to engage the ceramic body with a dental abutment for retaining the ceramic body to the dental abutment.

2. The method of claim 1, wherein the ceramic body is made of zirconium oxide or aluminum oxide.

3. The method of claim 1, wherein each of the plurality of the first type of ceramic particles is an opaque dental ceramic.

4. The method of claim 3, wherein the first temperature is 850-1000° C.

5. The method of claim 4, wherein the first temperature is 900-950° C.

6. The method of claim 3, wherein the second temperature is 850-1000° C.

7. The method of claim 6, wherein the first temperature is 900-950° C.

8. The method of claim 1, wherein the first sintering temperature and the second sintering temperature are the same.

9. The method of claim 1, wherein each of the plurality of the second type of ceramic particles has a Mohs hardness of at least 8.5.

10. The method of claim 1, wherein the composite porous layer has a thickness of 5-20 μm.

11. The method of claim 10, wherein the thickness is 10-20 μm.

12. The method of claim 1, wherein each of the plurality of the second type of ceramic particles has an average diameter of 0.1-0.8 μm.

13. The method of claim 12, wherein the average diameter is 0.1-0.15 μm.

* * * * *